United States Patent [19]
Ellis et al.

[11] Patent Number: 5,676,654
[45] Date of Patent: Oct. 14, 1997

[54] VARIABLE LENGTH BALLOON DILATATION CATHETER

[75] Inventors: Louis George Ellis, St. Anthony; Trac thanh Le, Columbia Heights, both of Minn.

[73] Assignee: SciMed Life Systems, Inc., Maple Grove, Minn.

[21] Appl. No.: 591,373

[22] Filed: Jan. 25, 1996

Related U.S. Application Data

[62] Division of Ser. No. 246,127, May 19, 1994, Pat. No. 5,514,093.

[51] Int. Cl.$^6$ ................................................. A61M 29/00
[52] U.S. Cl. ...................... 604/103; 604/96; 606/194
[58] Field of Search ............................ 604/96, 103, 264, 604/280; 606/192, 194

[56] References Cited

U.S. PATENT DOCUMENTS

| | | | |
|---|---|---|---|
| 3,896,815 | 7/1975 | Fettel et al. | 128/348 |
| 4,240,433 | 12/1980 | Bordow | 128/347 |
| 4,349,033 | 9/1982 | Eden | 128/660 |
| 4,479,497 | 10/1984 | Fogarty et al. | 128/344 |
| 4,493,711 | 1/1985 | Chin et al. | 604/271 |
| 4,526,175 | 7/1985 | Chin et al. | 128/344 |
| 4,564,014 | 1/1986 | Fogarty et al. | 128/344 |
| 4,606,347 | 8/1986 | Fogarty et al. | 128/344 |
| 4,630,609 | 12/1986 | Chin | 128/344 |
| 4,650,466 | 3/1987 | Luther | 604/95 |
| 4,744,366 | 5/1988 | Jang | 128/344 |
| 4,771,776 | 9/1988 | Powell et al. | 128/344 |
| 4,779,611 | 10/1988 | Grooters et al. | 128/4 |
| 4,820,270 | 4/1989 | Hardcastle et al. | 604/96 |
| 4,848,343 | 7/1989 | Wallsten et al. | 128/343 |
| 4,863,440 | 9/1989 | Chin | 604/271 |
| 4,875,480 | 10/1989 | Imbert | 128/343 |
| 4,958,634 | 9/1990 | Jang | 606/194 |
| 5,002,532 | 3/1991 | Gaiser et al. | 604/101 |
| 5,002,558 | 3/1991 | Klein et al. | 606/192 |
| 5,019,042 | 5/1991 | Sahota | 604/101 |
| 5,047,045 | 9/1991 | Arney et al. | 606/194 |
| 5,049,131 | 9/1991 | Deuss | 604/96 |
| 5,071,406 | 12/1991 | Jang | 604/96 |
| 5,074,845 | 12/1991 | Miraki et al. | 604/101 |
| 5,090,958 | 2/1992 | Sahota | 604/98 |
| 5,116,318 | 5/1992 | Hillstead | 604/96 |
| 5,137,512 | 8/1992 | Burns et al. | 604/96 |
| 5,147,377 | 9/1992 | Sahota | 606/194 |
| 5,160,321 | 11/1992 | Sahota | 604/96 |
| 5,163,927 | 11/1992 | Woker et al. | 604/271 |
| 5,178,608 | 1/1993 | Winters | 604/99 |
| 5,192,297 | 3/1993 | Hull | 606/195 |
| 5,217,434 | 6/1993 | Arney | 604/99 |
| 5,226,889 | 7/1993 | Sheiban | 604/101 |
| 5,246,421 | 9/1993 | Saab | 604/96 |
| 5,257,974 | 11/1993 | Cox | 604/96 |
| 5,275,622 | 1/1994 | Lazarus et al. | 623/1 |
| 5,364,356 | 11/1994 | Hofling | 604/96 |

*Primary Examiner*—Corrine M. McDermott
*Attorney, Agent, or Firm*—Nawrocki, Rooney & Sivertson, P.A.

[57] ABSTRACT

A variable length balloon catheter having an inner tubular member extending over the length thereof with a guide wire lumen therethrough. The distal waist of a balloon is affixed proximate the distal end of the inner tubular member while the proximal end or proximal waist of the balloon extends into and is slidably received within an outer tubular member. Means for sealing or preventing fluid flow between the proximal waist and inside diameter of the outer tubular member are provided. The means for sealing can include a passive or close tolerance seal assembly, an active seal assembly, or an axially elongatable membrane seal assembly. Axial movement of the inner tubular member varies the length of balloon extending distally beyond the distal end of the outer tubular member, thus determining inflated balloon length.

11 Claims, 9 Drawing Sheets

VARIABLE LENGTH BALLOON DILATATION CATHETER

This is a divisional of application Ser. No. 08/246,127 filed on May 19, 1994 now U.S. Pat. No. 5,514,093.

TECHNICAL FIELD

The present invention relates to apparatus for use in dilating occluded blood vessels. More particularly, it is directed to a balloon angioplasty catheter, wherein the length of the balloon may be selectively adjusted to match the length of the stenosis in the blood vessel to be treated when the balloon is inflated. The balloon angioplasty catheter incorporates a design with an active seal assembly, a passive seal assembly, or an axially elongatable membrane seal assembly which allows adjustment of the balloon size while preventing leakage of inflation fluid.

BACKGROUND OF THE INVENTION

Angioplasty procedures are widely recognized as efficient and effective methods for treating types of vascular disease. In particular, angioplasty is widely used for opening stenoses in the coronary arteries, although it is also used for the treatment of stenoses in other parts of the vascular system.

Apparatus for conducting angioplasty procedures generally include an inflatable balloon at their distal end. Typically in coronary procedures, a hollow guide catheter and/or guide wire are used in guiding the dilatation catheter through the vascular system to a location near the stenosis. Using fluoroscopy, assisted by the guide wire, the physician guides the dilatation catheter the remaining distance through the vascular system until the balloon is positioned across the stenosis. The balloon is then inflated by supplying fluid under pressure through an inflation lumen in the catheter to the balloon. The inflation of the balloon causes widening of the lumen of the artery to reestablish acceptable blood flow through the artery.

An over-the-wire (OTW) catheter design is well known in the art. The over-the-wire catheter is a catheter in which an inner tubular member, whether integral as in a multi-lumen tubular member or separate as in a coaxial design, provides a guide wire lumen so that the guide wire can provide a path to the stenosis, which may be tracked by the catheter as it is slidably received over the guide wire. In an over-the-wire design, the inner tubular member extends over the entire length of the catheter, and the lumen extending therethrough is isolated from the inflation fluid utilized to inflate the balloon.

Vascular occlusions to be treated by a balloon angioplasty apparatus can vary dramatically in size or length. With the variation in length of the occlusion, the area to be treated correspondingly varies in length. It is recognized as desirable to match the length of the balloon to be inflated during treatment as closely as possible to the length of the occlusion to be treated. This prevents expanding the balloon and pressing against a healthy artery wall. This requires, during a treatment, that the physician have on hand several catheters having different length balloons mounted thereon. It may also require the physician to exchange catheters in the middle of the treatment process so that a catheter of proper balloon length can be utilized. These factors can increase the cost of the procedure along with the time required for treatment.

The above problems can be overcome by incorporating a variable length balloon in a single dilatation catheter which allows selecting the length of the balloon at the time of or during treatment. Fogarty et al. (U.S. Pat. No. 4,564,014) and Saab (U.S. Pat. No. 5,246,421), the disclosures of which are incorporated herein by reference, disclose catheters incorporating a variable length balloon in a dilatation catheter.

Fogarty et al. discloses a catheter including an elongate elastomeric tube closed at its distal end and extending the full length of the catheter. A telescopic sheath is received around the elastomeric tube, which has a distal primary section which is moveable relative to the elastomeric tube and a proximal secondary section secured against movement relative to the elastomeric tube. A guide wire is disposed within and extends through the full length of the elastomeric tube with the guide wire having its distal end secured to the distal end of the tube, and proximal end extending from the proximal end of the tube. The length of the balloon is thus adjusted by moving the distal primary section of the sheath while maintaining the position of the elastomeric tube and proximal secondary section of the sheath.

To facilitate movement of the primary sheath section relative to the elastomeric tube, Fogarty et al. disclose that the elastomeric tube may be stretched lengthwise to reduce its diametrical cross-section by extending the guide wire which is fixed to the distal end of the elastomeric tube. The fixing of the guide wire to the distal end of the elastomeric tube, although aiding in adjusting the size of the balloon, prevents use as an over-the-wire device. Further, the movable primary sheath portion of Fogarty et al., if adjusted after insertion into the vessel, must be moved and in contact with the vessel wall to be treated. This may restrict or hinder movement of the sheath.

Saab also discloses an adjustable-length balloon dilatation catheter apparatus incorporating an adjustable sheath which is externally manipulated to partially surround and contain the dilatation balloon segment of the catheter while the catheter balloon segments are expanded during a treatment procedure. Saab discloses an adjustable sheath which is substantially coaxial with the catheter and substantially surrounds the catheter body, balloon, and catheter tip. Saab discloses that the sheath may run the full length of the catheter or be provided at the distal end of a relatively stiff, control catheter, with the latter being coaxially mounted relative to the balloon catheter. Thus, the sheath of Saab includes a separate tubular member to provide the sheath.

A known limiting factor for utilizing over-the-wire catheters is the profile of the balloon and shaft relative to the blood vessel lumen size being treated. Thus, there has been a continuing effort to reduce the balloon profile and shaft size of the dilatation catheter so that the catheter can reach and cross a very tight stenosis or a stenosis in a small vessel. Over-the-wire catheter designs have particularly been noted as limited due to a larger profile relative to other catheter designs, such as fixed wire devices or single operator exchange devices. This limitation is due to the need for a separate guide wire lumen running the full length of the catheter which is separate from the inflation lumen.

Although Saab discloses that the catheter of his invention can be modified or tuned to be compatible with virtually any catheter construction including, but not limited to, over-the-wire catheters, such modifications would compound the problems with profile. To modify Saab would require adding a tubular sleeve over the outside diameter of the outer tubular member of the catheter, and thus, increase the profile of the overall assembly.

SUMMARY OF THE INVENTION

The present invention is a catheter assembly, and more particularly, a balloon catheter assembly, wherein the length of the dilatation balloon may be varied. Preferably, the length of the balloon is set prior to insertion for treatment, however, it is recognized that adjustments to balloon length can be made subsequent to insertion for treatment. The catheter is an over-the-wire device which provides means for varying the length of the balloon without the addition of a moveable tubular sheath over the outside diameter of the catheter body.

With a standard over-the-wire coaxial catheter design, three general components are utilized. These include an inner tubular member, an outer tubular member and a balloon. The inner tubular member generally runs the full length of the catheter and includes a guide wire lumen extending therethrough in the annular space between the inner tubular member and outer tubular member. The outer tubular member is coaxially received over the inner tubular member and provides an inflation lumen therethrough. The outer tubular member generally terminates at its distal end axially spaced from the distal end of the inner tube. The balloon, having a distal waist and a proximal waist is connected at its distal end to the outside diameter of the inner tube proximate the distal end of the catheter and at its proximal end proximate to the distal end of the outer tubular member. With this general configuration, the annular space between the inner tubular member and outer tubular member is sealed and in fluid communication with the inside of the balloon. Further, the guide wire lumen is completely isolated from the inflation fluid.

The variable length balloon feature disclosed by Saab, if modified to include and over-the-wire design, would require the addition of an extra tubular member over the outer tubular member to form the moveable sleeve. In contrast, Applicants' variable length over-the-wire balloon dilatation catheter does not necessitate the addition of a third tubular member which increases the profile of the overall catheter. Rather, Applicants' over-the-wire catheter includes an inner tubular member which extends over the full length of the catheter and has a guide wire lumen extending therethrough. The balloon, more specifically the distal waist of the balloon, is secured or affixed to the outside diameter of the inner tubular member proximate the distal end of the catheter.

The catheter also includes an outer tubular member which is generally coaxially and slidably received over the inner tubular member. The distal end of the outer tubular member extends to and terminates at a location overlying the outside diameter of the balloon, but is not attached or secured proximate its distal end to the balloon. Rather, means for sealing the distal end of the outer tubular member from leakage of inflation fluid between the balloon outside diameter surface within the lumen of the outer tubular member and the inside surface of the outer tubular member, while allowing axial movement of the balloon relative to the outer tubular member, are provided. The means for sealing, as described below, for alternative embodiments, can include a passive seal assembly, an active seal assembly, or an axially elongatable membrane seal assembly.

A manifold is included at the proximal end of the catheter. The inner tubular member preferably extends proximally through the manifold. The inner tubular member may then be moved axially at the proximal end, the movement of which translates to the distal end of the inner tubular member where it is connected to the distal waist of the balloon. This arrangement allows adjustment of the position and length of the balloon relative to the distal end of the outer tubular member. Means are provided within the manifold to seal and prevent leakage of inflation fluid around the outside diameter of the inner tubular member at a point proximal of the inflation fluid connection or inlet port on the manifold.

Marker bands which are readily seen using fluoroscopy techniques are preferably incorporated proximate the distal end of the outer tubular member and within the balloon on the outside diameter of the inner tubular member within the distal portion of the balloon body. This arrangement allows determination of balloon length during treatment based on relative position of the marker bands. Markings on the inner tubular member in the area of its proximal end can also be utilized to confirm balloon length at a particular position.

A tip conforming to the inside and outside diameter of the distal end of the outer tubular member is preferably attached to the distal end thereof. The tip is preferably constructed from a pliable atraumatic material which generally conforms to the shape of the outside surface of the balloon as it is inflated and compressed against the inside diameter of the tip. Thus, during inflation, the tip flares outward and provides a smoother transition. Materials of construction can include polyurethane or a polyether blocked-amide (PEBA).

In a first embodiment, the variable length balloon catheter of the present invention includes a passive seal assembly. With this embodiment, the distal waist of the balloon is attached to the outside diameter surface of the inner tubular member proximate its distal end. The proximal waist of the balloon is sized to be slidably received within the lumen through the distal end of the outer tubular member. Further, the inside diameter of the proximal waist of the balloon is larger than the outside diameter of the inner tubular member. Thus, as assembled, a path for inflation fluid is defined into the interior of the balloon, but also a path around the outside diameter of the proximal waist of the balloon and out the distal end of the outer tubular member is also defined.

The passive seal is accomplished by adjusting the tolerance or distance between the outside surface or outside diameter surface of the proximal waist of the balloon and the inside surface of the outer tubular member to prevent leakage. Factors which influence the sufficiency of the passive seal include the space between the surfaces, along with the surface area of the close tolerance seal, in combination with the viscosity of the inflation fluid utilized and the inflation pressure. Thus, with this embodiment, the inner tubular member may be moved axially to adjust the length of the balloon with the proximal waist sliding within the distal portion of the outer tubular member until proper balloon size is achieved.

In a second alternative embodiment, an active seal assembly is incorporated in the catheter assembly. Several variations of an active seal assembly are disclosed herein. As with other embodiments, the inner tubular member passes through the entire length of the catheter, providing the guide wire lumen. The distal waist of the balloon is attached to the outside diameter surface of the inner tubular member proximate its distal end. The outer tubular member terminates at its distal end at a location over at least a portion of the outside diameter of the balloon. The balloon is not affixed or attached to the outer tubular member in any of the embodiments incorporating an active seal assembly to allow the inner tubular member to be moved axially with resultant adjustment of the length of balloon exposed for inflation.

The proximal waist or proximal region of the balloon is connected to the distal end of an active seal assembly. The active seal assembly can include an active sealing means which is at least indirectly connected to and moves axially with the inner tubular member when the balloon size is adjusted or an active sealing means which is in part affixed to the inside diameter surface of the outer tubular member near its distal end, wherein this part remains axially fixed during adjustment of the balloon size.

In a preferred embodiment, the proximal waist of the balloon is attached to at least one tubular member or seal tube which extends proximally and has a length at least equal to the desired length of adjustment of the balloon. The tubular member or seal tube extends proximally and is slidably received through the inside diameter of a seal member. The seal member has a generally circular opening for receiving the seal tube therethrough. The seal member can include an annular spacer which is sized to be slidable within the outer tubular member. The inside diameter of the spacer can have a first and a second cup-shaped seal mounted thereon. The seals are in turn affixed to the outside diameter of the seal tube. Each seal member is moveable from an inactive position to an active sealing position.

As assembled, a flow path for inflation fluid is created in the annular space between the inner tubular member and outer tubular member into the inside of the balloon. A path for inflation fluid is also created around the outside diameter of the seal member and spacer in the space between such surfaces and the inside diameter surface of the outer tubular member. Upon beginning inflation of the balloon, the cup-like seal member proximal to the spacer moves to an activated sealing position wherein the fluid path for leakage is reduced or eliminated so that the balloon may inflate. Likewise, upon beginning deflation of the balloon, the cup-like seal member distal of the spacer is activated by vacuum and prevents migration of body fluid into the inflation lumen.

As an alternative to the above seal assembly, an inflatable sealing membrane may be disposed on the seal tube. The entire seal assembly is thus moveable with respect to the outer tubular member. With this embodiment, inflation fluid is directed through ports through the wall of the seal tube into an inflatable bladder which expands to seal against the inside surface of the outer tubular member. As with the previous active seal, the path for inflation fluid between the surfaces of the expandable bladder and the inside surface of the outer tubular member is eliminated, thus preventing leakage past the outer surface of the proximal portion of the balloon between such surface and the inside surface of the outer tubular member. In a deflated state, the seal assembly slides axially with movement of the inner tubular member as the length of the balloon is adjusted.

With the expandable bladder seal assembly, a deflation seal may also be incorporated proximal to the bladder assembly. The deflation seal can be similar to the cup-like seal utilized in the previous embodiment, wherein upon withdrawing inflation fluid, the cup-like deflation seal is pressed against the seal tube to prevent migration of body fluid into the inflation lumen.

In an alternative embodiment, an axially elongatable membrane seal is incorporated into the catheter design. As with the active seal embodiments, the proximal end or proximal waist of the balloon is attached to the distal end of the axially elongatable membrane seal assembly. However, the proximal end of the axially elongatable membrane seal is affixed, either directly or indirectly, to the outer tubular member. Disposed between the distal end of the seal assembly and the point of connection on the proximal end of the outer tubular member, is an axially elongatable membrane. Thus, with this embodiment, a path for inflation fluid is established in the annular space between the outer tubular member and inner tubular member into the inside of the balloon. No path for flow of inflation fluid is provided through the seal area out the distal end of the outer tubular member because the axially elongatable membrane closes this fluid path. When the inner tubular member is moved axially, the axially elongatable membrane expands or contracts axially to compensate and allows the balloon to move axially and adjust the overall length of exposed balloon. The axially elongatable membrane can include a piece of elastic or stretchable tubing, a piece of tubing which readily folds over itself when contracted, or an accordion-shaped membrane which is folded to allow axial movement.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE INVENTION

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

Figure 1:
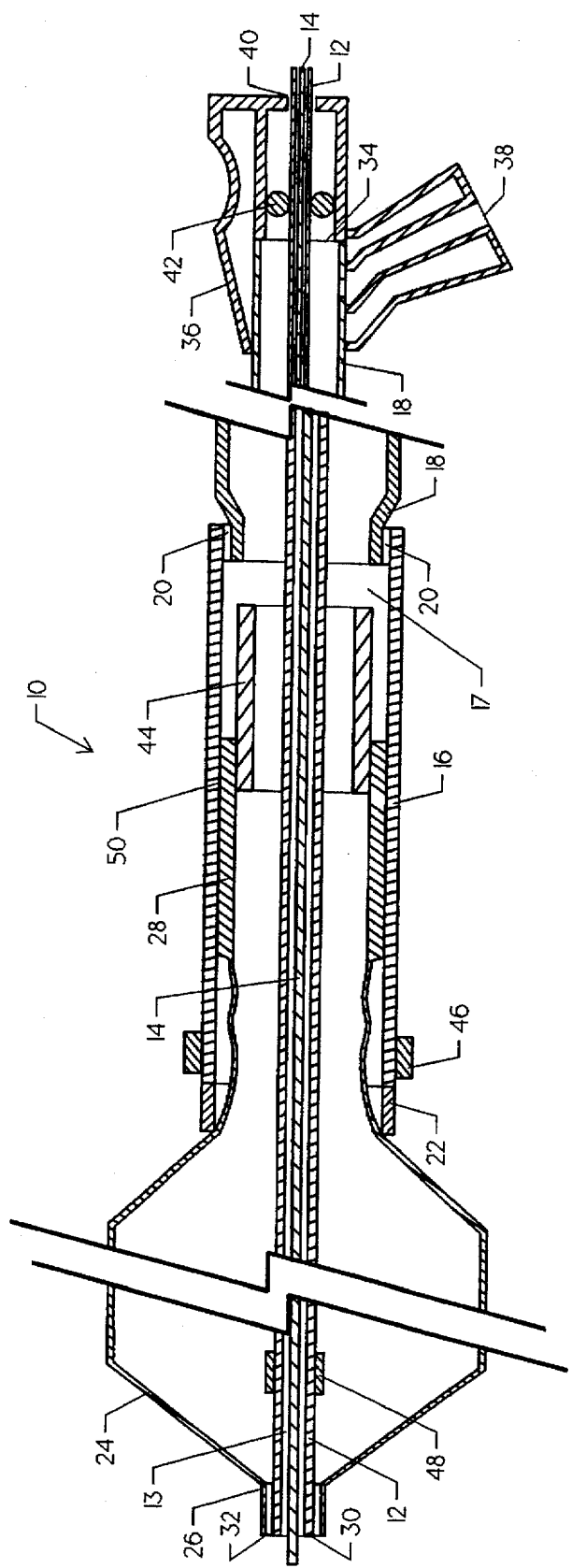
FIG. 1 is a longitudinal cross-sectional view of an over-the-wire catheter depicting a variable length balloon and a manifold assembly.
Figure 6:
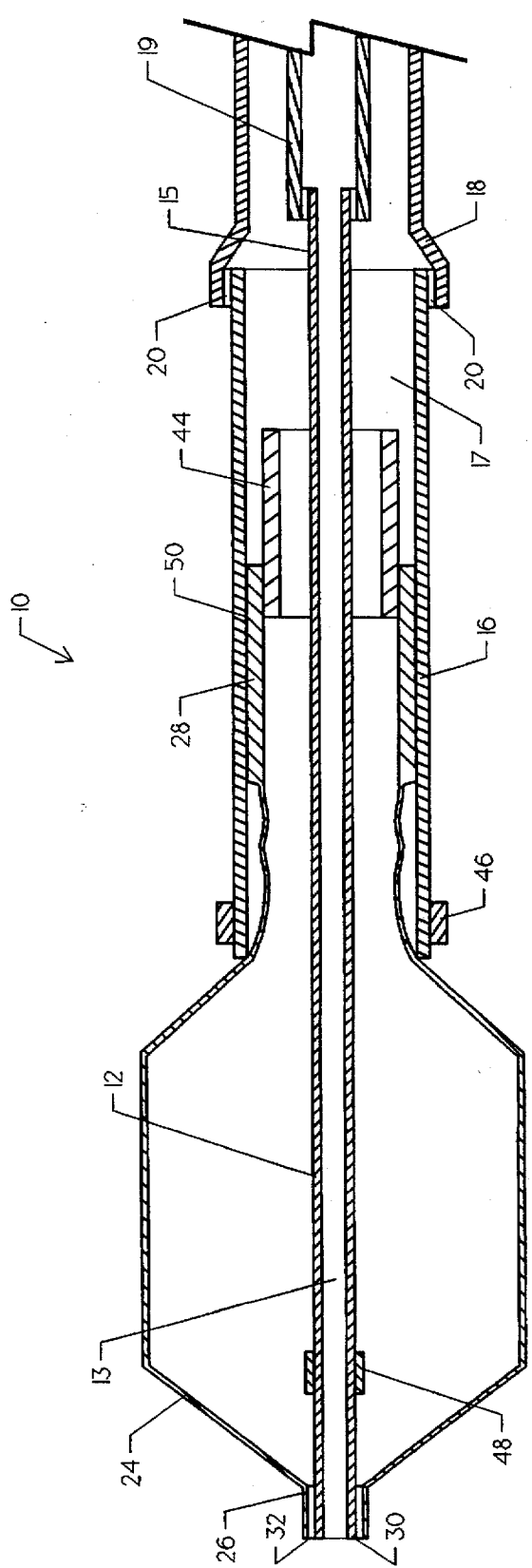
FIG. 6 is a longitudinal cross-sectional view of the distal portion of a variable length balloon catheter depicting a passive seal assembly.
Figure 7:
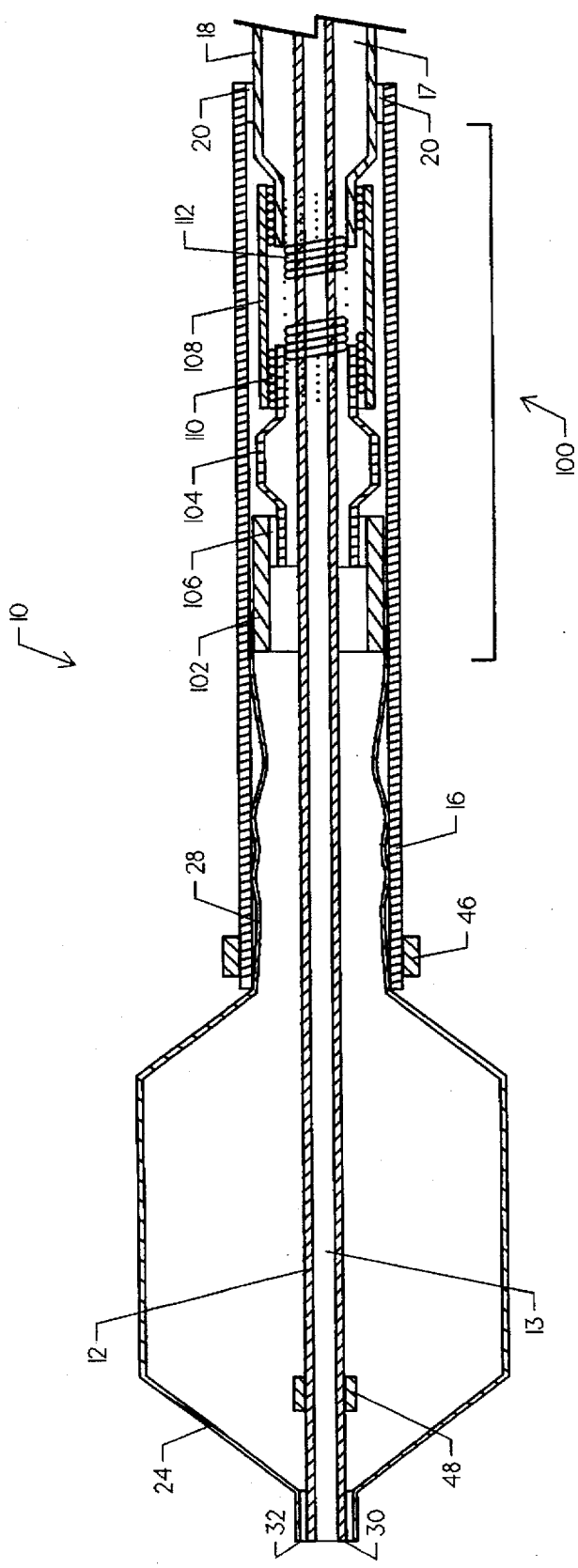
FIG. 7 is a longitudinal cross-sectional view of the distal portion of a variable length balloon catheter assembly incorporating an axially elongatable membrane seal assembly.
Figure 8:
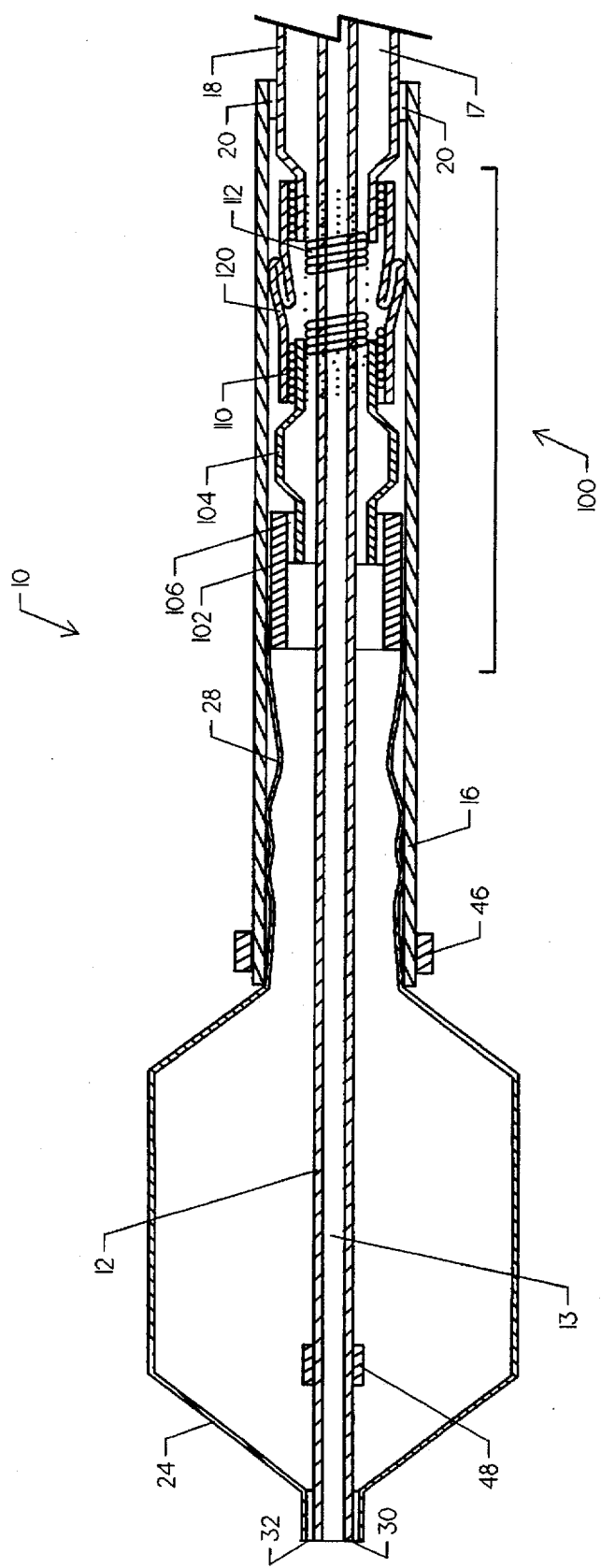
FIG. 8 is a longitudinal cross-sectional view of the distal portion of a variable length balloon catheter incorporating an alternative axially elongatable membrane seal assembly; and, FIG. 9 is a longitudinal cross-sectional view of the distal portion of a variable length balloon catheter incorporating a third alternative axially elongatable membrane seal assembly.
Figure 9:
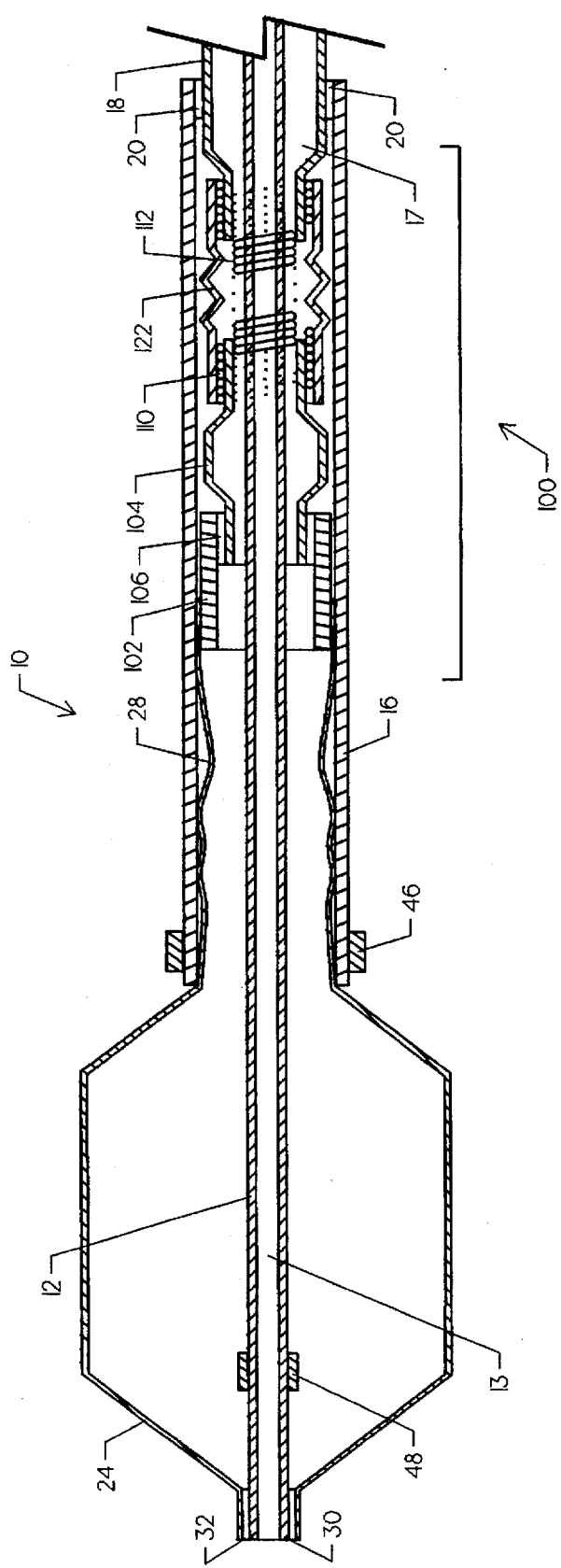

Now, referring to FIG. 1, a longitudinal cross-sectional view of an over-the-wire catheter assembly 10, having a variable length balloon 24 and manifold assembly 36 is depicted. The catheter assembly 10 depicted in FIG. 1 discloses several common structural features which are incorporated into all embodiments of the over-the-wire catheter design of the present invention. The main difference between the various embodiments is the type of seal assembly utilized to prevent flow of inflation fluid between the outside diameter surface of the unexposed portion of balloon 24 or a proximal waist 28 of the balloon 24 and an inside surface of an outer tubular member 16 into which the balloon 24 is slidably received. The various seal assemblies can include a passive seal assembly as depicted in FIGS. 1 and 6, an active seal assembly as depicted in FIGS. 2–5, or an axially elongatable membrane seal assembly as depicted in FIGS. 7–9. The details of these seal assemblies are discussed separately subsequent to a discussion of common features detailed with reference FIG. 1.

The basic construction of the catheter assembly 10 includes an inner tubular member 12, an outer tubular member 16, and an inflatable balloon 24. The inner tubular member 12 extends over the full length of the catheter assembly 10 and includes a guide wire lumen 13 extending axially therethrough. In use, the catheter assembly 10 is received over a guide wire 14 with the guide wire slidably received through the guide wire lumen 13. The guide wire 14, which is initially placed across a stenosis, allows the catheter assembly to be easily directed to the stenosis by tracking the guide wire 14.

The catheter assembly 10 includes an inflatable balloon 24. The inflatable balloon 24 can be manufactured from any suitable polymeric material, as generally known in the art. A preferred balloon material is SURLYN available from DuPont, which is preferably treated by irradiation. The balloon 24 is constructed to include a distal waist 26 extending distally from the inflatable or expandable portion of the balloon 24. The balloon also includes a proximal waist 28 which extends proximally from the inflatable or expandable portion of the balloon 24.

The inside diameter surface of the distal waist 26 is secured to the outside diameter surface of the inner tubular member 12 proximate its distal end 32. Adhesive means 30 can be utilized to secure the distal waist 26 to the inner tubular member 12.

The inner tubular member 12 can be a single tubular member which extends over the full length of the catheter assembly 10 or a multiple section tubular member. In one preferred embodiment, the inner tubular member 12 includes a proximal segment 19, which is manufactured from stainless steel hypo-tube and runs from the proximal end of the catheter distally approximately 100 cm. With this embodiment, the inner tubular member 12 also includes a distal portion 15 which is manufactured from polyimide having its proximal end connected to the distal end of the proximal inner hypo-tube with the lumen of each portion in fluid communication. The distal inner tube is preferably approximately 35 cm in length. The inside diameter, outside diameter and accompanying wall thickness of the inner tubular member 12 can be varied for the selected application. However, a preferred size includes an inside diameter ranging from 0.015 inches to 0.022 inches, and a wall thickness of 0.001 inches to 0.006 inches.

The proximal waist 28 of balloon 24 is slidably received within an outer tubular member 16. The outer tubular member 16 is thus coaxially received over the inner tubular member 12.

As depicted in FIG. 1, the distal end of the outer tubular member 16 terminates at a point over at least a portion of the expandable portion of the balloon 24. The distal end of the outer tubular member 16 then defines the length of balloon 24 exposed for inflation. The outer tubular member is, however, fixed in position and does not move in the axial direction as described below. The outer tubular member 16 can be a single tubular member which extends over substantially the entire length of the catheter assembly 10; however, in a preferred embodiment, the outer tubular member 16 is a multiple segment tubular member. Thus, in a preferred embodiment, the outer tubular member 16 includes a distal portion and a proximal portion 18. The distal end of the proximal portion is connected to the proximal end of the distal portion with through lumens in fluid communication. As described with respect to FIG. 5 below, the outer tubular member can include three segments. A preferred material of construction for the distal outer tubular member 16 is polyethylene teraphthalate (PET), while a preferred material of construction for the proximal portion 18 of the outer tubular member 16 is polyethylene. Preferred dimensions of the outer tubular member 16 will vary with application, however a wall thickness of about 0.002 inches is preferred.

The joint between the distal portion of the outer tubular member 16 and the proximal portion of the outer tubular member 18 can be of any known design. A lap joint is depicted in FIG. 1 with adhesive 20 bonding the two sections of the outer tubular member 16, 18.

A manifold assembly 36 is included at the proximal end of the catheter assembly 10. The outer tubular member 16 or proximal portion of the outer tubular member 18 terminates at its proximal end 34 within the manifold assembly 36. The outer tubular member includes a lumen which functions as an inflation lumen 17. The inflation lumen 17, near its proximal end 34, is in fluid communication with an inflation port 36 for receiving inflation fluid therethrough.

The inner tubular member 12 extends proximally through the manifold assembly 36 through a hole 40 in the proximal end of the manifold assembly. Thus, in use, the inner tubular member 12 may be moved axially by the person performing the angioplasty procedure from the proximal end of the catheter assembly 10. The movement of the inner tubular member 12 translates to the distal end of the inner tubular member 32 where it is connected to the distal waist 26 of the balloon 24. This arrangement allows adjustment of the position and length of the balloon 24 relative to the distal end of the outer tubular member 16.

Means for sealing 42 around the outside diameter of the inner tubular member 12 proximal of the inflation portion 38 of the manifold 36 are provided. This prevents leakage of inflation fluid out the hole 40 in the proximal end of the manifold assembly 36. The means for sealing 42 can include an O-ring, as depicted in FIG. 1, or any other seal or packing arrangement which are known in the art.

As previously stated, in use, a portion of the expandable portion of the balloon 24 is disposed within the inflation lumen 17 of the outer tubular member 16. Movement of the inner tubular member 12 in an axial direction determines the amount of balloon 24 exposed for inflation. When inflating the balloon 24, the outside surface of the balloon 24 presses against the distal end of the outer tubular member 16. In a preferred embodiment, an atraumatic tip 22 is attached to the distal end of the outer tubular member 16. The atraumatic tip 22 generally conforms to the shape of the outside surface of the balloon 24 as it expands. The tip 22 is preferably constructed from a pliable material, which is preferably a polyurethane or a polyether blocked-amide. During inflation, the tip flares outward and provides a transition from the balloon 24 to the outer tubular member 16.

A first marker band 46 can be located proximate the distal end of the outer tubular member. A second marker band 48 is preferably included within the balloon 24 and attached to the outside diameter surface of the inner tubular member 12. The marker bands are visible utilizing fluoroscopy techniques. This arrangement allows determination of balloon length during treatment based on relative position of the marker bands 46, 48. Alternatively, or in addition to the marker bands 46, 48, markings may be included on the outside surface of the inner tubular member 12 in the area of its proximal end extending outside the manifold assembly 36 which will confirm the balloon 24 length at a particular position of the inner tubular member 12.

In a first embodiment, the catheter assembly 10 of the present invention includes a passive seal assembly. A catheter assembly 10 incorporating such passive seal assembly is depicted in FIG. 1 and in detail in FIG. 6. Referring now to FIG. 6, the distal waist 26 of the balloon 24 is attached to the outside diameter surface of the inner tubular member 12 proximate its distal end 32. The proximal waist 28 of the balloon is sized to be slidably received within the lumen 17 of the outer tubular member 16. The inside diameter of the proximal waist 28 of the balloon 24 is larger than the outside diameter of the inner tubular member 12 which passes therethrough.

As assembled, the length of the balloon 24 can be varied by axially moving the inner tubular member 12. The proximal waist 28 of the balloon thus slides within the lumen 17 upon movement of the inner tubular member 12. As depicted in FIG. 6, the assembly creates a path for inflation fluid into the interior of the balloon 24. A path for fluid flow is also created around the outside diameter of the proximal waist 28 and out the distal end of the outer tubular member 16. By adjusting the tolerance or space 50 between the outside diameter of the proximal waist 28 of the balloon 24 and the inside diameter surface of the outer tubular member 16, a passive seal may be formed which greatly reduces or prevents leakage of inflation fluid through the space 50 between these members.

It is recognized that the passive seal could also be created by attaching the proximal waist 28 of the balloon 24 to the inside surface of a tubular member which is sized to serve the same function as previously described for the proximal waist 28 of the balloon 24. This tubular member would be sized so that the tolerance is sufficiently tight to form a seal. Factors which influence the sufficiency of a passive seal include the space between the surfaces along with the surface area or length of the close tolerance seal, in combination with the viscosity of the inflation fluid utilized and the desired inflation pressure.

As depicted in FIG. 6, a tubular support member 44 is depicted partially inserted into the proximal waist 28 of the balloon 24. The tubular support member 44 can be sized and utilized to help maintain the tolerance 50 between the surfaces and prevent buckling of the proximal waist 28 of the balloon. Further, the tubular support member 44 can be sized to keep the inner tubular member 12 aligned within the inflation lumen 17 when the inner tubular member is pushed axially to extend the balloon. The tubular support member 44 can include an inside diameter which allows the passage of inflation fluid while still reducing the amount of buckling as the inner tubular member 12 is moved axially.

In a second alternative embodiment, an active seal assembly is incorporated in the catheter assembly 10. Various embodiments of the active seal assembly are illustrated in FIGS. 2–5. An active seal assembly, is a seal assembly which, prior to inflation of the balloon 24, poses minimal or no restriction on fluid flow past the outside diameter of the proximal waist 28 of the balloon 24, and out the distal end of the outer tubular member 16 or minimal resistance to movement between slidably related elements. When inflation begins, the active seal is moved to a sealing position by the inflation fluid and prevents or greatly reduces leakage through the fluid flow path described above.

Figure 2:
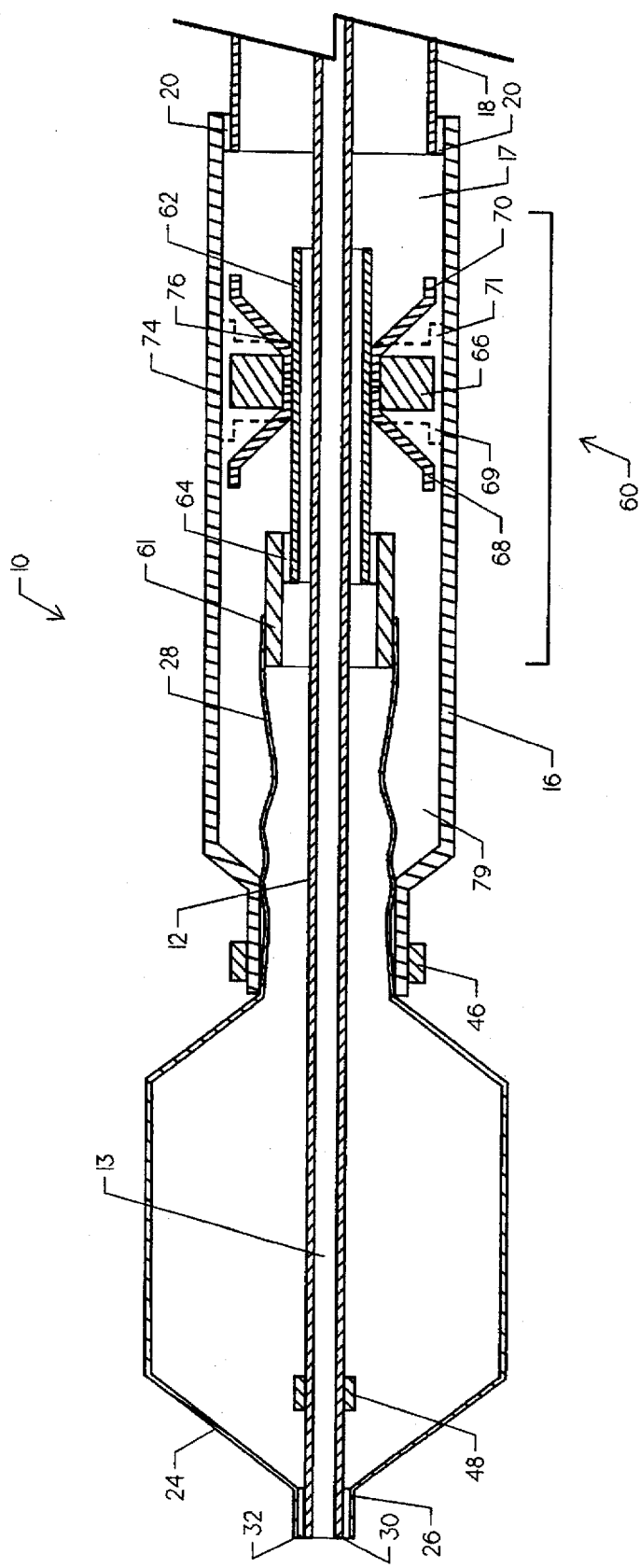
FIG. 2 is a longitudinal cross-sectional view of the distal portion of a variable length balloon catheter incorporating an active seal assembly.

Now, referring to FIG. 2, a cross-sectional view of a distal portion of a catheter assembly 10 is depicted incorporating one preferred active seal assembly 60. This active seal assembly incorporates cup-shaped, flexible seal elements 70, 68. The cup-shaped seal elements 68, 70 are moveable from an inactivated position to an activated position which is shown in phantom, based on fluid pressure.

As with other embodiments disclosed above, the inner tubular member 12 extends over the entire length of the catheter assembly 10 providing a guide wire lumen 13. The distal waist 26 of the balloon 24 is attached to the outside diameter surface of the inner tubular member 12 proximate its distal end 32. The outer tubular member 16 terminates at its distal end at a location such that at least a portion of the outside diameter of the balloon 24 is covered by the outer tubular member 16. The balloon 24 is not affixed or attached to the outer tubular member 16 in any of the embodiments incorporating an active seal assembly 60. This allows the inner tubular member 12 to be moved axially with resultant adjustment of the length of the balloon 24 for inflation.

The proximal waist 28 or proximal region of the balloon 24 is connected to the distal end of the active seal assembly 60. The active seal assembly 60 depicted in FIG. 2 moves axially with the inner tubular member 12 when the balloon 24 size is adjusted. It is, however, recognized that an active seal assembly could also include a portion which is affixed to the inside diameter surface of the outer tubular member 16 near its distal end, wherein this part could remain axially fixed during adjustment of the balloon 24 position and size.

With the embodiment depicted in FIG. 2, the proximal waist 28 of the balloon 24 is attached to a seal tube 62. The connection to the seal tube 62 may be direct or indirect. As depicted in FIG. 2, the indirect attachment includes an intermediate adapter 61 which has a distal end connected to the proximal waist of the balloon 28 and a proximal end connected to the distal end of the seal tube 62 by adhesive 64. The intermediate adapter tube 61 is utilized to compensate for differences in inside diameter of the proximal waist of the balloon relative to the outside diameter of the seal tube 62. The seal tube 62 has a length at least equal to the desired length of adjustment of the balloon.

The seal tube 62 extends proximally from the proximal waist 28 of the balloon 24 and is slidably received through a seal member 66 which is slidably received with the lumen 17 of the outer tubular member 16. The seal member 66, in a preferred embodiment, includes a spacer which is generally cylindrical in shape and has a bore therethrough. The spacer can be sized with close tolerance to the diameter of the lumen 17 of the outer tubular member 16. The spacer is thus slidable within the outer tubular member, however, leakage around the spacer during inflation is minimized.

The spacer of the seal member 66 has mounted thereon a first cup-shaped seal element 70 and a second cup-shaped seal element 68. As depicted in FIG. 2, the first seal element 70 has a section of reduced diameter which is adhered to the surface of the bore. In turn, the opposing surfaces of the seal element 70 are affixed or connected to the outside diameter of the seal tube 62. The seal element 70 extends proximally and expands radially to a larger diameter to form the cup-shaped portion of the seal element 70. Likewise, the second seal element 68 has an area of reduced diameter which is adhered to the bore of the spacer. The opposing surface is also affixed or connected to the outside diameter of the seal tube 62. The second seal element 60 extends distally and expands radially to form the cup-shaped portion of the seal element 68. Each seal element 70, 68 is moveable from an inactive position to an active sealing position.

As assembled, a flow path for inflation fluid is created in the annular space between the inner tubular member 12 and outer tubular member 16 into the inside of the balloon 24. However, a path for inflation fluid is also created around the outside diameter of the spacer and seal elements 68, 70 in the space 74 between such surface and the inside diameter surface of the outer tubular member 16. Upon beginning inflation of the balloon 24, the cup-like seal element 70 proximal to the spacer moves to an activated sealing position (shown in phantom) wherein the fluid path for leakage is reduced or eliminated so that the balloon 24 may inflate. The seal element 70, in an activated position 71, prevents leakage around the outside diameter of the spacer and seal element 68, 70.

Similar to the inflation cycle, upon beginning deflation of the balloon 24, the cup-like seal element 68 which is distal of the spacer 76 is moved to an activated position under vacuum. The seal element moves to an activated position 69 as indicated in phantom in FIG. 2. This seal prevents migration of body fluid into the inflation lumen in the space between the outside diameter of the spacer and seal elements 68, 70 and the inside diameter of the outer tubular element 16.

Although the details of a specific active seal member have been described, it is recognized that variations in the construction are possible within the scope of the present invention. For example, the cup-like seal elements 70, 68 could be replaced with various configurations, such as a lip seal. Further, a preferred material of construction is polyurethane, however, any pliable polymeric or elastomeric material could be utilized as long as it is sufficiently pliable to move to an activated position upon beginning inflation or deflation of the balloon 24. The spacer can be manufactured from any polymeric material which is compatible. The seal tube 62 is preferably manufactured from polyimide, however, other polymeric materials are suitable.

As depicted in FIG. 2, the distal outer tube 16 is necked down proximate its distal end. Applicants have found that necking down the distal outer tube 16 prevents or reduces creeping of the balloon in the distal direction during inflation. Movement of the balloon 24 during inflation would alter the selected length of the balloon 24. Thus, the necked portion helps control and maintain the selected size of the balloon during the inflation cycle. However, with this design, a void area 79 is created.

The void area 79, with the design shown in FIG. 2, cannot be purged from the proximal end of the catheter. The purging is necessary to make sure that there is no air present in the void area 79. To overcome this problem, a purge tap can be located on the inside diameter of the outer tubular member 16 proximal to the seal tube 62 over its normal range of travel. The purge tap can include a nub or spacer which maintains a fluid path around the seal element 68, 70 when the inner tubular member 12 is pulled fully in the proximal direction. When the inner tubular member 12 is extended distally into its normal range of movement, the purge tab would no longer be across the seal element, and would thus, not interfere with the normal operation once the purging cycle is complete. To maintain use of the full useable length of the balloon 24, the seal tube 62 can be lengthened to allow for full travel of the balloon, and an additional length to include the purge tap. In preferred embodiments, the usable balloon length can be from slightly over 0 to 100 mm, with a preferred useable length of 10 mm to 40 mm. When the inner tubular member 12 is fully retracted, the distal outer tube can act as a balloon protector. This obviates the need for a separate protector.

Figure 3:
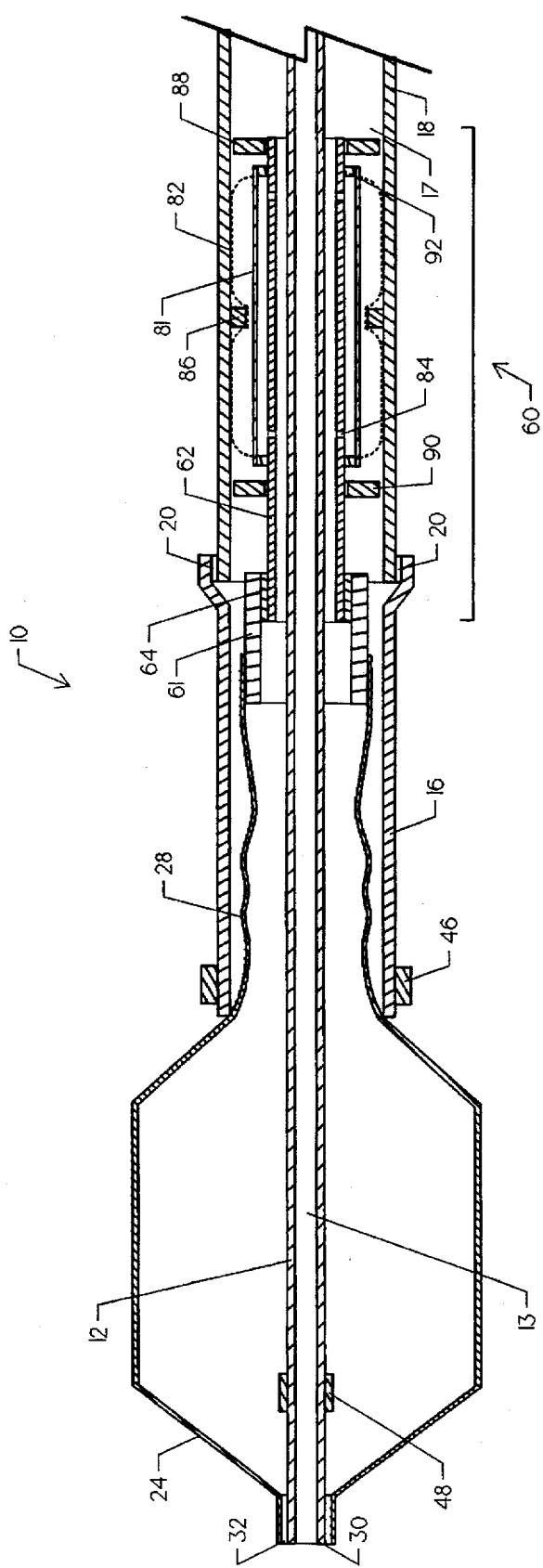
FIG. 3 is a longitudinal cross-sectional view of the distal portion of a variable length balloon catheter incorporating an alternative active seal assembly.

Now, referring to FIG. 3, an alternative active seal assembly is depicted which incorporates an inflatable sealing membrane 81. The entire seal assembly 60 is disposed on the seal tube 62. As with the previous embodiment, the seal tube extends proximally and is connected to the proximal waist 28 of the balloon 24. An adapter 61 can be incorporated to compensate for differences in radial dimensions on the proximal waist 28 of the balloon 24 and the seal tube 62. Adhesive means 64 may be utilized to connect the subassemblies. The entire seal assembly 60 is moveable with respect to the outer tubular member 16. Movement of the inner tubular member results in equal movement of the seal assembly 60.

The inflatable sealing membrane 81 surrounds a portion of the seal tube 62. The seal tube includes at least one inflation port 84 which communicates inflation fluid from inside the seal tube 62 into the seal membrane 81 for inflation of that membrane.

Prior to beginning inflation of the balloon 24, the inner tubular member 12 is slidable axially, and the uninflated membrane 81 possess little or no resistance to such movement. A distal travel stop 90 mounted on the outside diameter of the seal tube 62, in conjunction with an intermediate travel stop 86 mounted on an inside diameter of the outer tubular member 16, can be included to limit axial movement in the proximal direction. A proximal travel stop 88 can also be included which works with the intermediate travel stop 86 to limit travel in the distal direction. The travel stops also restrict fluid flow to some degree around the outside of the seal assembly 60 so that inflation fluid will more readily flow into the seal membrane 81 when inflation begins.

In operation, the beginning of inflation of balloon 24 results in the movement of the seal membrane 81 from an inactive position to an activated position 82, depicted in phantom. Thus, the seal element 82 comes into contact with the inside diameter surface of the outer tubular member 16. Proper spacing prior to inflation and after inflation can be adjusted by utilizing spacers 92 to determine the membrane location prior to inflation. The expandable bladder 81 can be manufactured from any suitable elastomeric material. A preferred material of construction is polyurethane.

Figure 4:
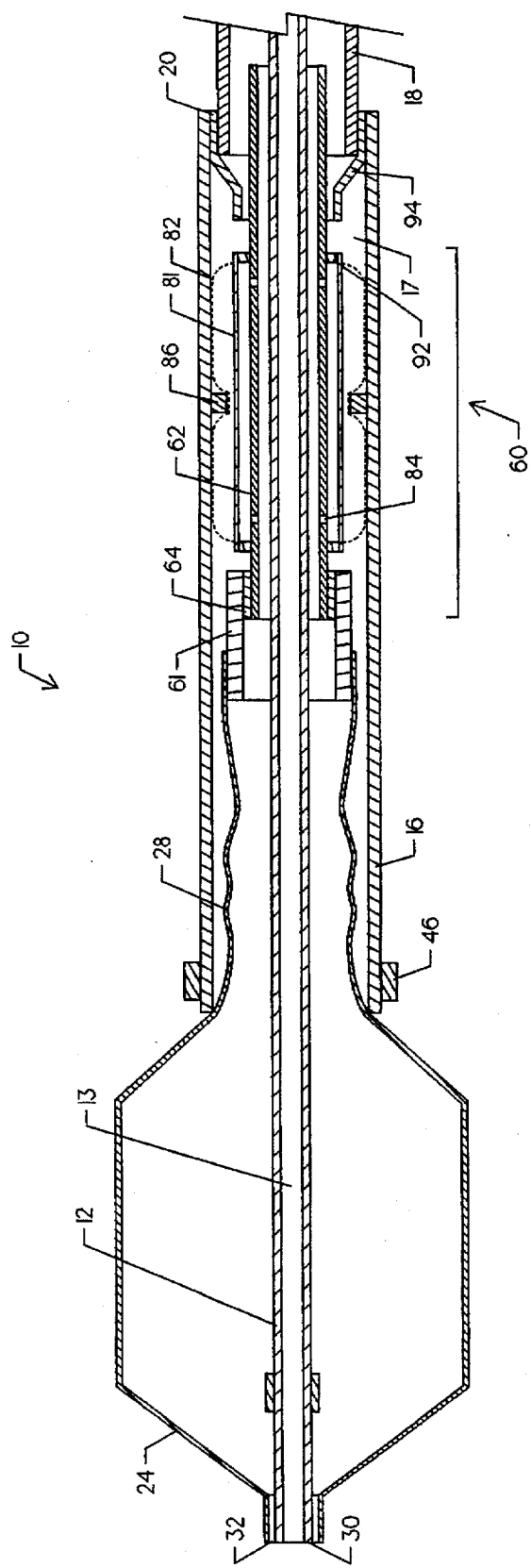
FIG. 4 is a longitudinal cross-sectional view of the distal portion of a variable length balloon catheter assembly incorporating a third alternative active seal assembly.

Now, referring to FIG. 4, a related embodiment to that depicted in FIG. 3, is illustrated. The embodiment incorporates the feature of the expandable bladder assembly 60 in FIG. 3. However, a cup-shaped seal element 94 is also included. The cup-like element 94 is similar to the structure of the seal elements 70, 68 depicted in FIG. 2. A single element 94 is mounted proximal to the expandable bladder seal assembly 60. The seal element 94 is activated by vacuum during the deflation of the balloon to prevent migration of body fluids into the inflation lumen. As shown, the element 94 is mounted at the joint between segments of the outer tubular members 16, 18.

Figure 5:
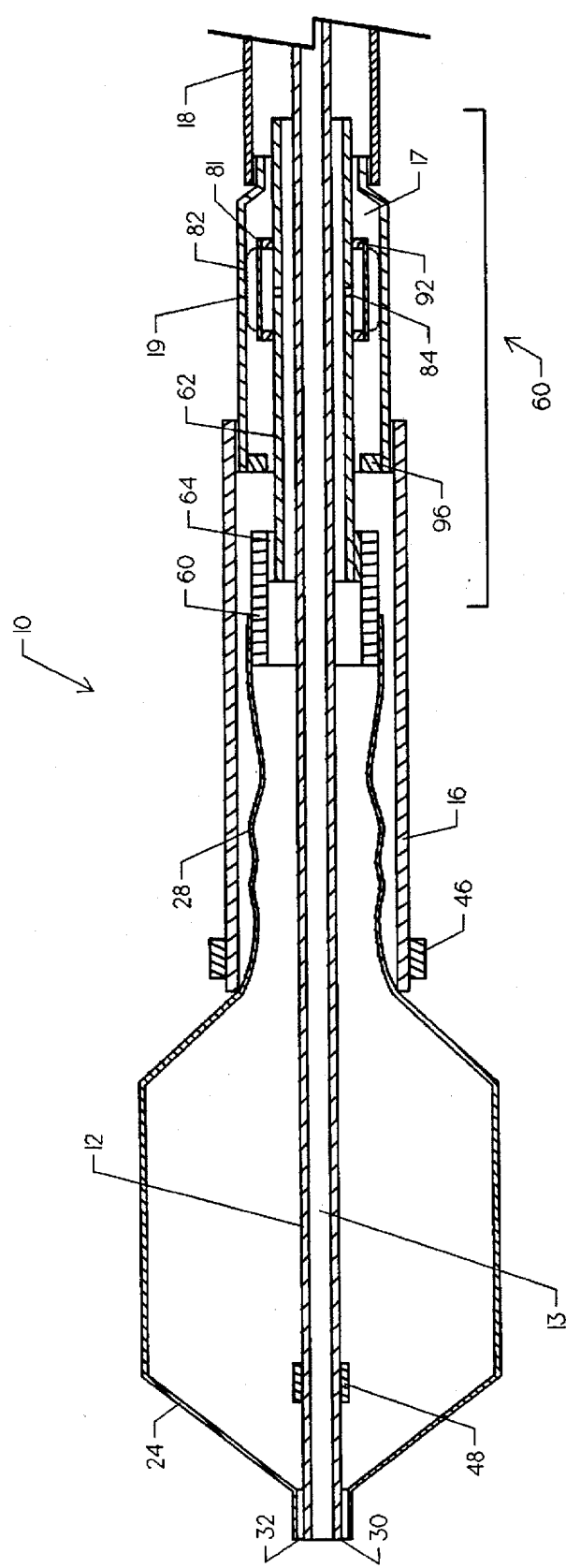
FIG. 5 is a longitudinal cross-sectional view of the distal portion of a variable length balloon catheter assembly depicting a fourth alternative active seal assembly.

Another alternative expandable bladder assembly 60 is depicted in FIG. 5. With this embodiment, the outer tubular member includes at least three segments. The distal outer tubular segment 16 and the proximal outer tubular segment 18 are depicted, as with other embodiments. However, an intermediate outer tubular segment 19 is included wherein the seal element 60 is disposed. Again, the seal tube 62 extends proximally from the proximal waist 28 of the balloon 24. A spacer 60 can be included to adjust for diameters. The seal tube 62 includes at least one fluid communication port 84 from the inside diameter of the seal tube 62 into the bladder assembly 81. The bladder 81 is mounted around the outside diameter of the seal tube 62 and can include spacers 92 to properly position the outside diameter of the inflatable member 81 relative to the inside diameter of the intermediate outer tubular member 19. Movement of the seal in the inactivated or non-inflated position is unimpeded. A distal travel stop 96 can limit distal movement of the seal element. Moving in the proximal direction, as depicted in FIG. 5, is limited by the necked down wall area of the intermediate tubular member 19. A travel stop could, alternatively, be utilized for this same purpose.

As with the previous embodiment, the travel stop 96 limits fluid flow upon beginning inflation of the balloon so that fluid is directed into the membrane 81 for expansion. As the membrane expands to an expanded state 82, the membrane seals against the inside diameter surface of the intermediate tubular member 19.

In a third alternative embodiment, an axially elongatable membrane seal 100 is incorporated into the catheter 10 of the present invention. As with the active seal embodiments discussed above, the proximal end or proximal waist 28 of the balloon 24 is attached to the distal end of the seal assembly. An axially elongatable membrane seal assembly 100 is depicted in FIG. 7. With this embodiment, the proximal end of the axially elongatable membrane seal assembly 100 is attached to or affixed to the outer tubular member 18 at a point proximal to the seal assembly 100. Thus, the seal assembly depicted in FIG. 7 does not freely move in the axial direction as the length of balloon 24 exposed is altered. Instead, an axially elongatable membrane 108 is disposed between the distal end of the seal assembly 100 and the point of connection on the proximal end to the outer tubular member 18. The axially elongatable membrane 108 elongates or contracts with movement of the inner tubular member to allow for movement of the balloon. As described below, this membrane can include a stretchable tubular member, an accordion shaped tubular member, or a tubular member which readily folds over itself when contracted. These embodiments are depicted in FIGS. 7–9.

Now, referring to FIG. 7, the proximal waist 28 of the balloon is connected to a spacer 102 which is utilized to adjust for differences in dimension. The proximal end of the spacer 102 is adhesively connected 106 to the distal end of the adapter 104. The proximal end of the adaptor has a proximal waist on which spring elements 110 are coiled. The distal end of the cylindrical axially elongatable membrane 108 is attached to spring elements 110. The elongatable membrane 108 extends proximally to a point of connection on the outer tubular member 18. Again, spring elements 110 may be wrapped around the outside diameter of the neck of the outer tubular member 18 with the membrane 108 attached thereto. Spring elements 112 can also be included around the outside diameter of inner tubular member 12 within the seal region 100. The spring elements 112 around the inner tubular member 12 help prevent buckling of the inner tubular member 12 when pushed distally to lengthen the balloon.

The spring elements 110 at the point of attachment of the membrane 108 improve elongation of the element 108 when the inner tubular member is moved in the distal direction.

Although a spacer 102 and adapter 104 are depicted in FIG. 7, it is recognized that these elements can be eliminated if the proximal waist 28 of the balloon 24 and seal elements are sized accordingly.

A preferred material of construction for the axially elongatable membrane 108 is polyurethane. Preferred dimensions include a 0.030 inch inside diameter and a 0.002 inch wall thickness.

Now, referring to FIG. 8, a modified embodiment of the axially elongatable membrane seal 100 is depicted. The stretchable membrane 108 depicted in FIG. 7 is replaced with an axially elongatable membrane 120 which is designed to fold over itself as it is compressed by retraction of the inner tubular member 12 in the proximal direction. A preferred material of construction for this membrane is SURLYN. Preferred dimensions include a 0.001 inch wall thickness and a 0.035 inch inside diameter.

Referring now also to FIG. 9, a further modification of the embodiments described above for FIGS. 7 and 8 are depicted. The stretchable membrane 108 is replaced with an accordion-shaped membrane 122 which allows for travel of the inner tubular member 12 in the axial direction. The accordion-shaped membrane 122 folds and unfolds in response to movement in either direction. A preferred material of construction for the accordion-shaped membrane is SURLYN. Preferred dimensions include a 0.001 inch wall thickness and a 0.035 inch inside diameter.

Embodiments of the variable length balloon catheter 10 depicted and described above can also be utilized for the placement of stents within a blood vessel. Stents may be pressure or balloon expandable, self-expandable, or a combination thereof. The last stent is described in U.S. Ser. No. 08/246,320, filed on even date herewith, entitled "Improved Tissue Supporting Devices". Examples of balloon or pressure expandable stents can be found in Hess (U.S. Pat. No. 5,197,978), Palmaz (U.S. Pat. No. 4,733,665), Wiktor (U.S. Pat. No. 5,133,732) and Gianturco (U.S. Pat. No. 5,041,126). Self-expandable stents are described in U.S. Pat. Nos. 4,655,771; 4,954,126 and 5,016,275, all to Wallsten. To deliver a self-expandable or combination stent, for example, referring to FIG. 4, a shoulder or collar could be placed around the outside diameter of the spacer 61. The spacer can extend radially to approximately equal the inside diameter of the outer tubular member 16. A stent can then be loaded over the uninflated balloon 24 and abut the shoulder on spacer 61. In this way, the balloon may be axially extended prior to inflation within the blood vessel to place the stent over the desired location. Upon placing the stent, the balloon may be retracted so that the proper length of balloon is exposed within the stent with subsequent inflation to either expand the stent or properly press the expandable stent against the vessel wall.

Balloon or pressure expandable stents may be delivered in the manner described above or may simply be crimped down on the distal end of the balloon. In this case, the balloon and stent can be axially extended until the stent is outside the sheath. The balloon and the stent can then be expanded.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A variable length balloon catheter having a distal and a proximal end comprising:
   a. an inner tubular member having a proximal and distal end extending from the distal end of said catheter to the proximal end of said catheter having a guide wire lumen extending therethrough;
   b. an outer tubular member, generally co-axially received over said inner tubular member forming an inflation lumen therebetween, said outer tubular member terminating at a distal end proximate said distal end of said inner tubular member;
   c. an expandable balloon element having a distal waist, a proximal waist and an expandable portion therebetween, said distal waist sealably connected to said inner tubular member proximate its distal end and said proximal waist extending over and having an inside diameter larger than the outside diameter of said inner tubular member to allow fluid flow therebetween, at least a portion of said expandable balloon element slidably received within a distal portion of said inflation lumen; and,
   d. an active seal assembly co-axially disposed about said inner tubular member within said inflation lumen between said inner tubular member and said outer tubular member, wherein said active seal assembly prevents leakage of inflation fluid around said expandable balloon element during inflation.

2. The catheter of claim 1, wherein said active seal assembly comprises:
   a. a seal tube, having a lumen therethrough and a distal end connected to said proximal waist of said balloon, said seal tube extending proximally generally co-axially over a portion of said inner tubular member, said seal tube having an inside diameter larger than said outside diameter of said inner tubular member to allow fluid flow therebetween; and,
   b. an elastomeric seal member disposed on the inside surface of said outer tubular member having a bore therethrough, wherein said seal tube is slidably received through said bore, said elastomeric seal member, in response to flow of inflation fluid being moveable from a non-sealing position to a sealing position to prevent flow between said seal member and said seal tube.

3. The catheter of claim 2, wherein said elastomeric seal member includes at least one cup-like elastomeric element.

4. The catheter of claim 1, wherein said active seal assembly comprises:
   a. a seal tube, having a lumen therethrough and a distal end connected to said proximal waist of said balloon, said seal tube extending proximally generally co-axially over a portion of said inner tubular member, said seal tube having an inside diameter larger than said outside diameter of said inner tubular member to allow fluid flow therebetween, said seal tube also including at least one inflation port through the wall thereof; and,
   b. an expandable bladder disposed around and sealably connected to said seal tube over said inflation port wherein in response to flow of inflation fluid said bladder expands radially to contact and seal against the inside surface of said outer tubular member to prevent flow between said expandable bladder and said inside surface of said outer tubular member.

5. The catheter of claim 4, further comprising a first at least one stop mounted on the inside surface of said outer tubular member in operable relation to a second at least one stop mounted on said seal tube, wherein said stops limit axial movement of said inner tubular member.

6. The catheter of claim 2, further comprising a deflation seal disposed proximal of said expandable bladder, and disposed co-axially within and sealably attached to said outer tubular member inside surface, wherein upon applying vacuum said deflation seal engages the outside surface of said inner tubular member.

7. A variable length balloon catheter having a distal and a proximal end comprising:
   a. an inner tubular member having a proximal and distal end extending from the distal end of said catheter to the proximal end of said catheter having a guide wire lumen extending therethrough;
   b. an outer tubular member, generally co-axially received over said inner tubular member forming an inflation lumen therebetween, said outer tubular member terminating at a distal end proximate said distal end of said inner tubular member;
   c. an expandable balloon element having a distal waist, a proximal waist and an expandable portion therebetween, said distal waist sealably connected to said inner tubular member proximate its distal end and said proximal waist extending over and having an inside diameter larger than the outside diameter of said inner tubular member to allow fluid flow therebetween, at least a portion of said expandable balloon element slidably received within a distal portion of said inflation lumen; and,
   d. an axially elongatable membrane having a distal end and a proximal end, said membrane having a proximal end sealably connected to said outer tubular member and a distal end sealably connected to the proximal waist of said balloon, wherein said membrane expands and contracts in response to axial movement of said inner tubular member such that axial expansion of said membrane extends said distal waist of said balloon from said distal end of said outer tubular member.

8. The catheter of claim 7, further comprising an adapter tubular member having a distal end sealably connected to the proximal waist of said balloon and a proximal end sealably connected to the distal end of said elongatable membrane.

9. The catheter of claim 8, wherein said axially elongatable membrane is an elastomeric tubular element.

10. The catheter of claim 8, wherein said axially elongatable membrane is a thin wall tubular element that folds over itself when contracted.

11. The catheter of claim 8, wherein said axially elongatable membrane is an accordion-shaped tubular element which folds and unfolds when contracted or expanded.

* * * * *